(12) United States Patent
Mielekamp et al.

(10) Patent No.: US 9,839,482 B2
(45) Date of Patent: Dec. 12, 2017

(54) ABLATION PLANNING WITH LESION COVERAGE FEEDBACK

(75) Inventors: Peter Maria Mielekamp, Veldhoven (NL); Alessandro Guido Radaelli, Oirschot (NL); Niels Jan Noordhoek, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 474 days.

(21) Appl. No.: 14/342,444

(22) PCT Filed: Sep. 10, 2012

(86) PCT No.: PCT/IB2012/054687
§ 371 (c)(1),
(2), (4) Date: Mar. 3, 2014

(87) PCT Pub. No.: WO2013/038324
PCT Pub. Date: Mar. 21, 2013

(65) Prior Publication Data
US 2014/0228835 A1   Aug. 14, 2014

Related U.S. Application Data

(60) Provisional application No. 61/533,815, filed on Sep. 13, 2011.

(51) Int. Cl.
*A61B 18/14* (2006.01)
*A61B 19/00* (2006.01)
(Continued)

(52) U.S. Cl.
CPC .............. *A61B 19/50* (2013.01); *A61B 34/10* (2016.02); *A61B 34/25* (2016.02); *G06T 19/20* (2013.01);
(Continued)

(58) Field of Classification Search
CPC ........ A61B 2034/104; A61B 2034/107; A61B 2034/252; A61B 2034/254;
(Continued)

(56) References Cited

U.S. PATENT DOCUMENTS 6,575,969 B1   6/2003   Rittman et al.
7,343,030 B2   3/2008   Sawyer
(Continued)

FOREIGN PATENT DOCUMENTS

EP   1791070 A2   5/2007
WO   2011080666 A1   7/2011

*Primary Examiner* — Michael Peffley

(57) ABSTRACT

A tumor targeting ablation planning device and method include providing a predetermined ablation profile and a segmented tumor to be treated in an ablation procedure. A contour of the segmented tumor is generated and the predetermined ablation profile is overlapped with a part of the segmented tumor to form an overlapping region, which is identified. Further, a predetermined safety factor is applied to at least a part of the at least one segmented tumor in the overlapping region to generate a modified overlapping region. Parts of the overlapping region that are arranged outside the modified overlapping region are determined as overlapping portions. A display is configured to: display the contour of the segmented tumor, display the predetermined ablation profile overlapped with the at least part of the segmented tumor in the overlapping region, and display the overlapping portions in relation with the contour and the ablation profile as virtual planning ablation result.

17 Claims, 18 Drawing Sheets

(51) Int. Cl.
*G06T 19/20* (2011.01)
*A61B 18/00* (2006.01)
*A61B 18/02* (2006.01)
*A61B 18/18* (2006.01)
*A61B 34/10* (2016.01)
*A61B 34/00* (2016.01)
*A61B 90/00* (2016.01)

(52) U.S. Cl.
CPC ....... *A61B 18/1477* (2013.01); *A61B 18/1815* (2013.01); *A61B 2018/00577* (2013.01); *A61B 2018/0293* (2013.01); *A61B 2018/1425* (2013.01); *A61B 2018/1869* (2013.01); *A61B 2034/104* (2016.02); *A61B 2034/107* (2016.02); *A61B 2034/252* (2016.02); *A61B 2034/258* (2016.02); *A61B 2090/374* (2016.02); *A61B 2090/376* (2016.02); *A61B 2218/00* (2013.01)

(58) Field of Classification Search
CPC . A61B 18/1477; A61B 18/1815; A61B 19/20; A61B 19/50; A61B 2018/00577; A61B 2018/0293; A61B 2018/1425; A61B 2018/1869
See application file for complete search history.

(56) References Cited

U.S. PATENT DOCUMENTS

| | | |
|---|---|---|
| 7,871,406 B2 | 1/2011 | Nields et al. |
| 2007/0129626 A1 | 6/2007 | Mahesh et al. |
| 2009/0142740 A1 | 6/2009 | Liang et al. |
| 2010/0063496 A1 | 3/2010 | Trovato et al. |
| 2011/0015628 A1 | 1/2011 | Dalal et al. |

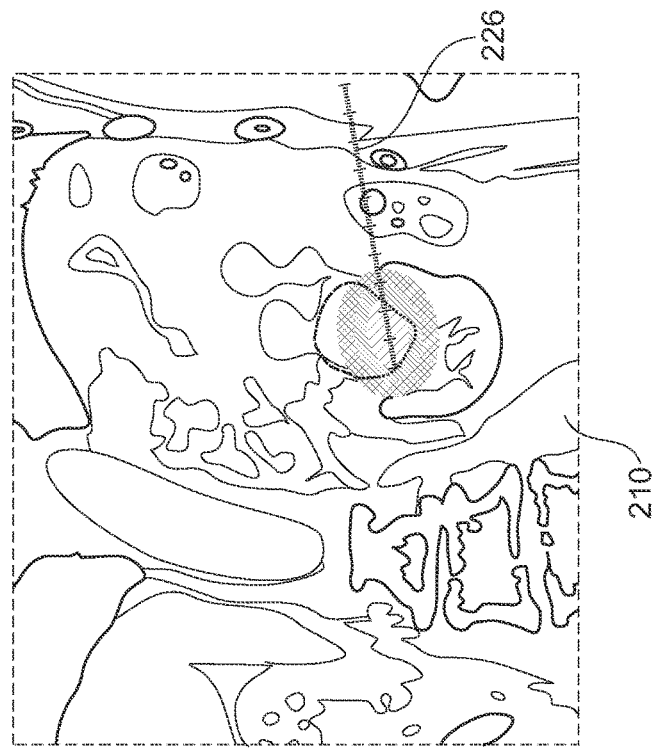
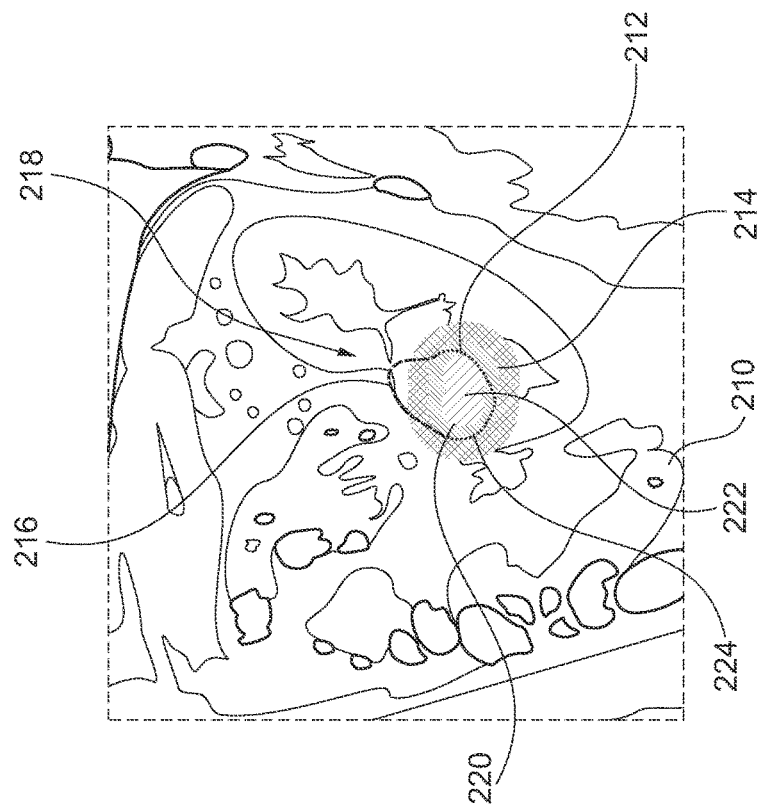
Fig. 8a
Fig. 8b

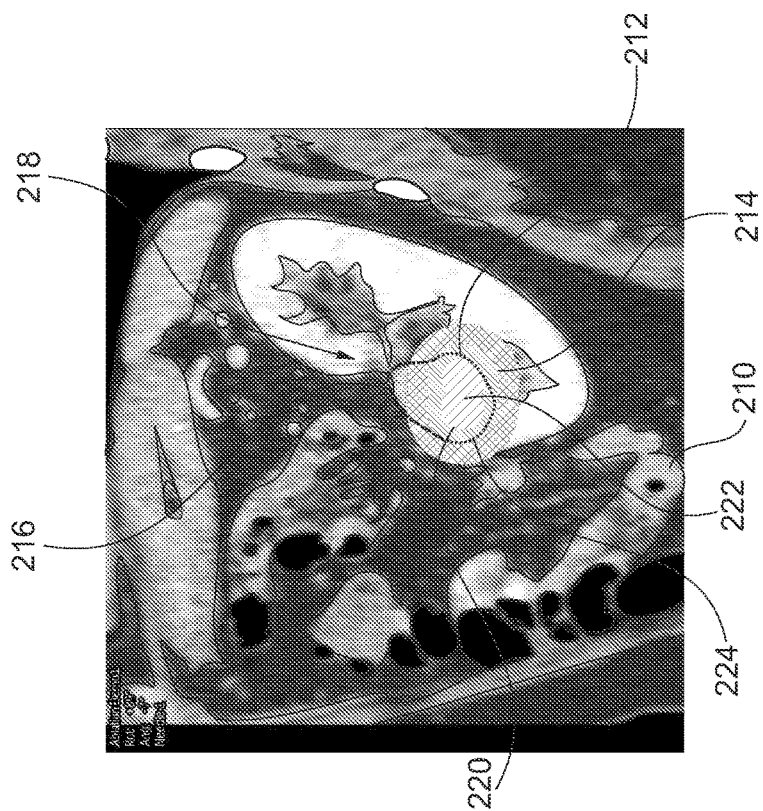
Fig. 14b
Fig. 14a

ABLATION PLANNING WITH LESION COVERAGE FEEDBACK

CROSS-REFERENCE TO PRIOR APPLICATIONS

This application is the U.S. National Phase application under 35 U.S.C. §371 of International Application Serial No. PCT/IB2012/054687, filed on Sep. 10, 2012, which claims the benefit of U.S. Application Ser. No. 61/533,815, filed on Sep. 13, 2011. These applications are hereby incorporated by reference herein.

FIELD OF THE INVENTION

The present invention relates to tumour targeting ablation planning, and in particular to a planning device for tumour targeting ablation planning, a medical system for tumour targeting ablation, a method for tumour targeting ablation planning, as well as a computer program element, and a computer readable medium.

BACKGROUND OF THE INVENTION

Minimally invasive image-guided tumour ablation technology is becoming a viable treatment option for a variety of unresectable, or un-dissectionable, tumours, for example. The aim in tumour ablation is the complete kill of the tumour cells. Therefore, the size, shape and location of an ablation zone are evaluated during a planning step before the intervention. For example, WO 2010/0063496 A1 describes a method for planning a tumour ablation procedure. However, tumour targeting ablation planning is often planned freehand and the procedure outcome may vary from operator to operator.

SUMMARY OF THE INVENTION

Thus, there is a need to provide a facilitated and improved image-based planning method.

The object of the present invention is solved by the subject-matter of the independent claims, wherein further embodiments are incorporated in the dependent claims.

It should be noted that the following described aspects of the invention apply also for the planning device, the medical system, the method for tumour targeting ablation planning, the computer program element and the computer readable medium.

According to a first aspect of the present invention, a planning device for tumour targeting ablation planning is provided, comprising a processing unit, an interface unit, and a display unit. The interface unit is configured to provide at least one segmented tumour in a 3D data set to be treated in an ablation procedure. The interface unit is further configured to provide a predetermined ablation profile. The processing unit is configured to generate a contour of the segmented tumour, to overlap the predetermined ablation profile with at least a part of the at least one segmented tumour, to identify an overlapping region, and to apply a predetermined safety factor at least to a part of the overlapping region to generate a modified overlapping region. The processing unit is further configured to determine parts of the overlapping region that are arranged outside the modified overlapping region as critical overlapping portions. The display unit is configured to display the contour of the segmented tumour, to display the predetermined ablation profile overlapped with at least a part of the at least one segmented tumour, and to display the critical overlapping portions in relation with the contour and the ablation profile as virtual planning ablation result.

According to an exemplary embodiment of the present invention, the processing unit is configured to add a predetermined first safety margin to the at least one segmented tumour to generate a dilated contour of the tumour, and to determine the parts of the dilated contour arranged outside the ablation profile as critical dilated contour portions. The display unit is configured to display the dilated contour and to indicate the critical dilated contour portions.

According to an exemplary embodiment of the invention, the processing unit is configured to subtract a predetermined second safety margin from the predetermined ablation profile to generate a limited planned ablation profile, and to determine the parts of the contour arranged outside the planned ablation profile as critical contour portions. The display unit is configured to display the planned ablation profile and to indicate the critical contour portions.

According to an aspect of the invention, a user interface is provided which indicates and displays a contour of a segmented tumour and a predetermined ablation profile. Further, critical overlapping portions are displayed in relation with the contour and the ablation profile as virtual planning ablation result, wherein the critical overlapping portions relate to parts of an overlapping region which are arranged outside a modified overlapping region, which relates to an overlapping region to which a safety factor has been applied.

According to a second aspect of the present invention, a medical system for tumour targeting ablation is provided, comprising an image acquisition unit, a planning device according to one of the above described aspects and embodiments, and an ablation unit. The image acquisition unit is configured to provide the 3D data set from which the tumour is segmented. The planning device is configured to provide an ablation path. The ablation unit is configured to apply the ablation procedure to the tumour.

According to a third aspect of the present invention, a method for tumour targeting ablation planning is provided, comprising the following steps:
a) providing at least one segmented tumour in a 3D data set to be treated in an ablation procedure;
b) generating and displaying a contour of the segmented tumour;
c) providing and displaying a predetermined ablation profile to overlap with at least a part of the at least one segmented tumour;
d) identifying an overlapping region;
e) applying a predetermined safety factor to at least a part of the overlapping region to generate a modified overlapping region, wherein parts of the overlapping region arranged outside the modified overlapping region are determined as critical overlapping portions; and
f) displaying the critical overlapping portions in relation with the contour and the ablation profile as virtual planning ablation result.

According to an exemplary embodiment, the predetermined ablation profile is adjustable by the user in its size, shape, and/or location. The steps b) to f) may be repeated to provide updated information to the user.

According to an exemplary embodiment of the invention, step e) comprises adding a predetermined first safety margin to the at least one segmented tumour to generate a dilated contour of the tumour; displaying the dilated contour; determining the parts of the dilated contour arranged outside the ablation profile as critical dilated contour portions. In step f), the critical dilated contour portions are indicated in the display.

According to an exemplary embodiment, step e) comprises subtracting a predetermined second safety margin from the predetermined ablation profile to generate a limited planned ablation profile; displaying the planned ablation profile; determining the part of the contour arranged outside the planned ablation profile as critical contour portions. In step f), the critical contour portions are indicated in the display.

According to an exemplary embodiment, the segmented tumour is displayed in on overlaid manner together with image data of a surrounding region.

According to an exemplary embodiment, a planned insertion path of an ablation target for the tumour targeting ablation is shown.

According to a further aspect of the present invention, a planning setup is provided in which the contour of the segmented tumour is brought into relationship with an ablation profile such that, by comparing the spatial regions occupied by the segmented tumour on one side, and covered by the ablation profile on the other side, the overlapping areas are determined. Further, by applying a predetermined safety factor, an extra ablation is provided to ensure a successful ablation of the complete necrosis of the entire tumour as well as a boundary margin around the tumour, or lesion, respectively. The extra ablation is necessary to treat microscopic cancer cells surrounding the tumour and to minimize the effect of imprecise applicator placement. According to an aspect of the present invention, by identifying those parts of the overlapping region arranged outside the margin considering the extra ablation by applying the predetermined safety factor, which parts of the overlapping region are referred to as critical overlapping portions, it is possible to provide an immediate feedback to the user in form of the virtual planning ablation result in which the critical overlapping portions are displayed in relation with the contour of the segmented tumour and the ablation profile. Thus, the user is provided with an interactive tool to optimize the planned ablation procedure before starting with the procedure itself.

For example, the user can adjust the size, shape, and/or location of the ablation profile and is immediately provided with updated planning ablation result information.

These and other of the invention will become apparent from and elucidated with reference to the embodiments described hereinafter.

BRIEF DESCRIPTION OF THE DRAWINGS

Exemplary embodiments of the invention will be described in the following with reference to the following drawings.

FIGS. 8A to 8B show an example for a displayed virtual planning ablation result according to the present invention.

FIGS. 14 to 18 show the line drawings of FIGS. 8 to 11 and 13 with photographic images.

DETAILED DESCRIPTION OF EMBODIMENTS

Figure 1:
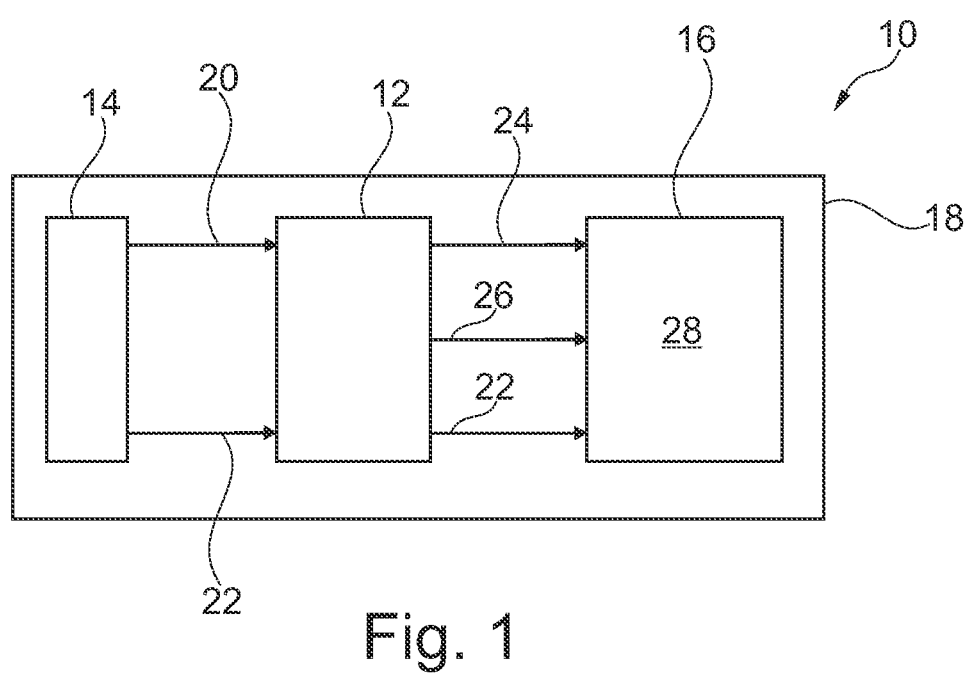
FIG. 1 shows a planning device for tumour targeting ablation planning according to an exemplary embodiment of the present invention.

Before referring to the figures, some aspects are described in the following: Due to advances in imaging technology and the availability of highly controllable medical devices, minimally invasive image-guided tumour ablation technology is becoming an important treatment option for tumours. Currently, three ablation methods are used. First, radiofrequency ablation (RF) involves the use of electrical currents in the range of radiofrequency waves through a needle that heats and destroys cancer cells. The objective is to ablate the tumour and the rim of normal tissue around its edges. Second, microwave ablation (MW) induces thermal coagulation of tissue using microwaves. The ablation diameter is less than with radiofrequency ablation, but multiple needles can be used to achieve larger ablation volumes. Tissue ablation is achieved in shorter time than compared to radiofrequency ablation. Third, cryoablation is the use of freezing gas circulating within a needle in a tumour to kill cancer cells in freeze/thaw cycles. Several needles can be used in parallel and the development of the ablative ice ball can be monitored with CT/MR/cone-beam CT, or the like. The two main challenges in tumour ablation are to achieve an accurate and reproducible applicator placement and a complete kill of intermediate and large tumours. The size of tumours has repeatedly been shown as a predictor of treatment failure. One method for the creation of larger, more complete zone of ablation is to use multiple, overlapping ablations. This requires multiple, precise applicator placements such that the ablation zones overlap. A successful ablation requires complete necrosis of the entire tumour as well as, for example, a 0.5 to 1 cm margin around the lesion. The area of the tumour and its safety margin are also referred to as the planned target volume (PTV). The size, shape, and location of the ablation zone are evaluated before interventions during the planning step. The user defines the optimal location, number and orientation of applicators to achieve a complete coverage of the PTV. The resulting ablation volume is referred to as the planned ablation volume (PAV).

The term "tumour targeting" relates to the step during an ablation procedure that involves placement of an applicator, for example, radiofrequency electrode or cryoablation probe, into the tumour. Ideal conditions for accurate targeting include clear delineation of the tumour(s) and the surrounding anatomy through multi-planar image reconstructions, coupled with real-time imaging to visualize the applicator's and interactive capabilities.

In an automatic radiofrequency ablation planning method, coverage of an arbitrary shaped planning target volume with multiple overlapping ellipsoid ablations is computed. However, as a problem with such automatic applicator planning method, these are generally too inflexible to tackle all the specific placement constraints. In user guided planning methods, instead of using rudimental linear measurements to define ablation areas over the targeted tumour, ablation profiles may be provided by the manufacturing companies that are shown at the tip of the planned needle path in a planning procedure. However, during the ablation planning process, the clinical user continuously interprets the clinical information to identify the boundaries of the tumour and its margin.

According to the present invention, a flexible and reliable ablation treatment planning and tumour targeting method is proposed that provides a separation of concerns by allowing the user to first segment the tumour regions and then to use this information to plan ablation applicator positioning using tumour coverage feedback.

For example, tumour segmentation can be fully automatic or user-assisted. The 3D interactive tumour segmentation may be based on a set of image adaptive radial functions with linear combinations of spatially localized kernels that follows image features. For example, during the segmentation, a number of control points with radius and direction (grow/shrink) are used to control the 3D segmentation process. The output of the segmentation can be a 3D vector list of the segmented volume.

According to a further example, the segmentation can be an integrated part of the ablation planning tool. Therefore, the input control list may be stored and reused in a simple XML format. In this way based on a very small descriptive segmentation receipt stored next to the volume data, the segmentation can be simply saved, loaded, re-modified, and reused, for instance in case of overlay.

FIG. 1 illustrates a planning device 10 for tumour targeting ablation planning. The device 10 comprises a processing unit 12, an interface unit 14, and a display unit 16. The planning device 10 is schematically indicated by a surrounding frame 18, indicating an integrated design of the planning device 10. Of course, the individual parts of the planning device 10 may also be provided as separate components.

The interface unit 14 is configured to provide at least one segmented tumour in a 3D data set 20 to be treated in an ablation procedure. The interface unit 14 is further configured to provide a predetermined ablation profile 22.

The processing unit 12 is configured to generate a contour 24 of the segmented tumour, to overlap the predetermined ablation profile with at least a part of the at least one segmented tumour, to identify an overlapping region, to apply a predetermined safety factor at least to a part of the overlapping region to generate a modified overlapping region, and to determine parts of the overlapping region that are arranged outside the modified overlapping region as critical overlapping portions 26.

The display unit 16 is configured to display the contour 24 of the segmented tumour, to display the predetermined ablation profile 22 overlapped with at least a part of the at least one segmented tumour 20, and to display the critical overlapping portions 26 in relation with the contour 20 and the ablation profile 22 as virtual planning ablation result 28.

The interface unit 14 may be configured for adjusting the predetermined ablation profile 22 by the user in its size, shape, and/or location. The processing unit 12 may be configured to repeat the identification of an overlapping region, the application of a predetermined safety factor to generate an updated modified overlapping region, and the determination of parts of the overlapping region that are arranged outside the modified overlapping region as critical overlapping portions. The display unit 16 may be configured to provide updated ablation planning information.

The ablation profile may comprise a concatenation of a set of multiple profiles that are operated by multiple (mostly parallel) ablation needles.

The processing unit 12 may be configured to add a predetermined first safety margin to the at least one segmented tumour to generate a dilated contour of the tumour, and to determine the parts of the dilated contour arranged outside the ablation profile as critical dilated contour portions. The display unit 16 may be configured to display the dilated contour, and to indicate the critical dilated contour portions.

The processing unit 12 may be configured to subtract the predetermined second safety margin from the predetermined ablation profile to generate a limited planned ablation profile, and to determine the parts of the contour arranged outside the planned ablation profile as critical contour portions. The display unit 16 may be configured to display the planned ablation profile and to indicate the critical contour portions.

Figure 2:
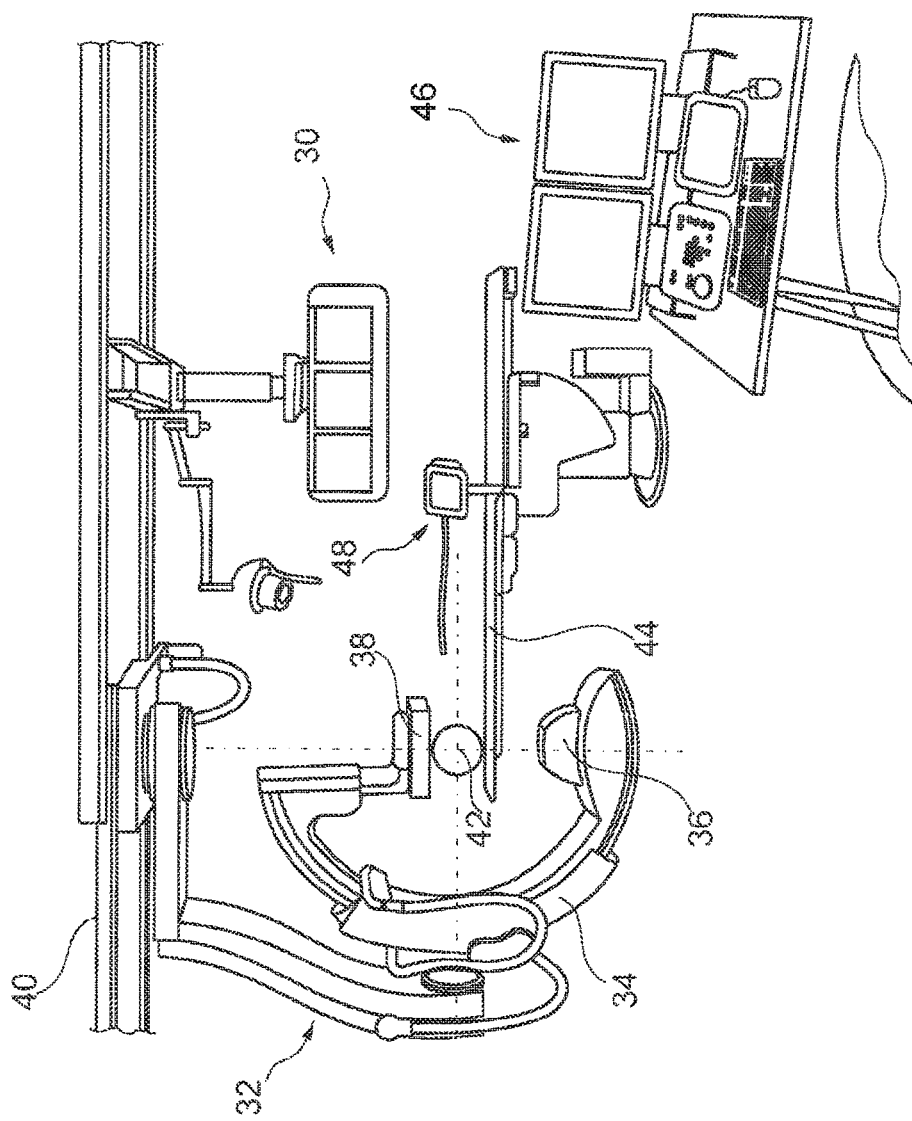
FIG. 2 shows a medical system for tumour targeting ablation according to an exemplary embodiment of the present invention.

In FIG. 2, a medical system 30 for tumour targeting ablation is schematically shown. The medical system 30 comprises an image acquisition unit 32, for example a C-arm structure 34 with an X-ray source 36 at one end of a C-arm and a detector 38 at the other end of the C-arm. The C-arm structure 34 is suspended from a ceiling 40 in such a way that sliding and rotational movement of the C-arm with source and detector in relation to an object 42 are possible, which object indicated with a sphere, but which can also be a patient (not further shown). Further, a patient table 44 is shown, as well as a planning device 46, which is provided according to one of the above described exemplary embodiments. Further, an ablation unit 48 is schematically indicated.

The image acquisition unit 32 is configured to provide the 3D data set from which the tumour is segmented. The planning device 46 is configured to provide an ablation path. The ablation unit 48 is configured to apply the ablation procedure to the tumour.

The image acquisition unit may be an X-ray imaging device, for example a C-arm structure, as shown, but also a CT system with a gantry, or other X-ray imaging systems. The image acquisition unit may also be an MRI-imaging device or other.

Figure 3:
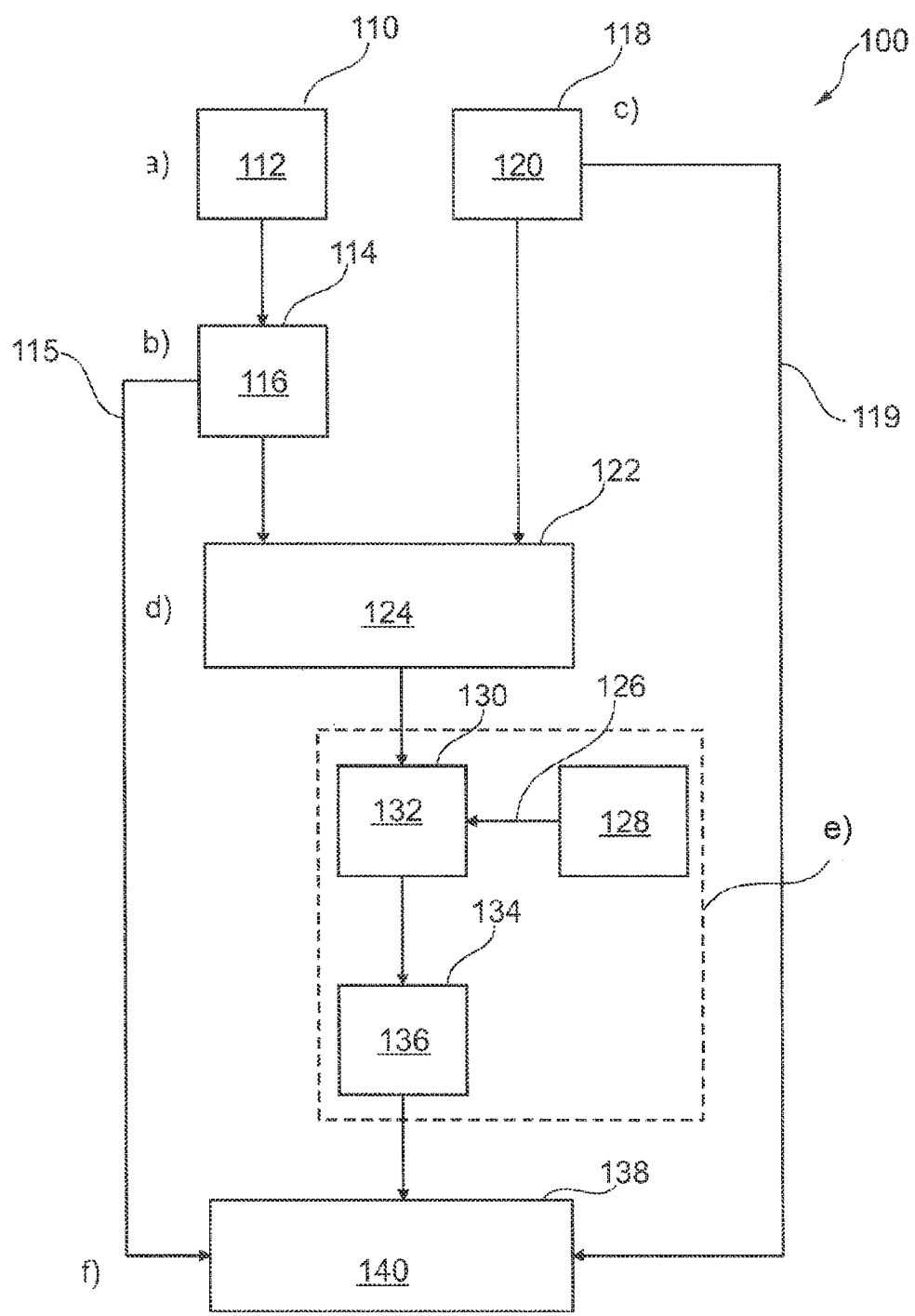
FIG. 3 schematically illustrates basic steps of a method for tumour targeting ablation planning according to an exemplary embodiment of the present invention.

FIG. 3 schematically illustrates basic steps of a method 100 for tumour targeting ablation planning. In a provision step 110, at least one segmented tumour in a 3D data set 112 is provided, wherein the segmented tumour is to be treated in an ablation procedure. In a generation and display step 114, a contour 116 of the segmented tumour is generated and displayed. The displaying is indicated with a first arrow 115 (described below). In a providing and displaying step 118, a predetermined ablation profile 120 is provided and displayed to overlap with at least a part of the at least one segmented tumour, wherein the displaying aspect of this step is indicated with a second arrow 119. Next, in an identification step 122, an overlapping region 124 is identified. In an application step 126, a predetermined safety factor 128 is applied to at least a part of the overlapping region 124 to generate, in a generation step 130, a modified overlapping region 132. Parts of the overlapping region arranged outside the modified overlapping region are determined in a determination step 134 as critical overlapping portions 136. Further, in a display step 138, the critical overlapping portions 136 are displayed in relation with the contour 116, as indicated with first arrow 115, and the ablation profile 120, as indicated with second arrow 119, as virtual planning ablation result 140.

The provision step 110 is also referred to as step a), the generation and display step 114 as step b), and the provision and display step 118 as step c), the identification step 122 as step d), the application step 126 as step e), and the display step 138 as step f).

It is further noted that the method also relates to a method for operating a device comprising similar steps as the method for tumour targeting ablation planning.

The ablation profile may be shown in cross-section with isotherms representing the ablation zones.

Figure 4:
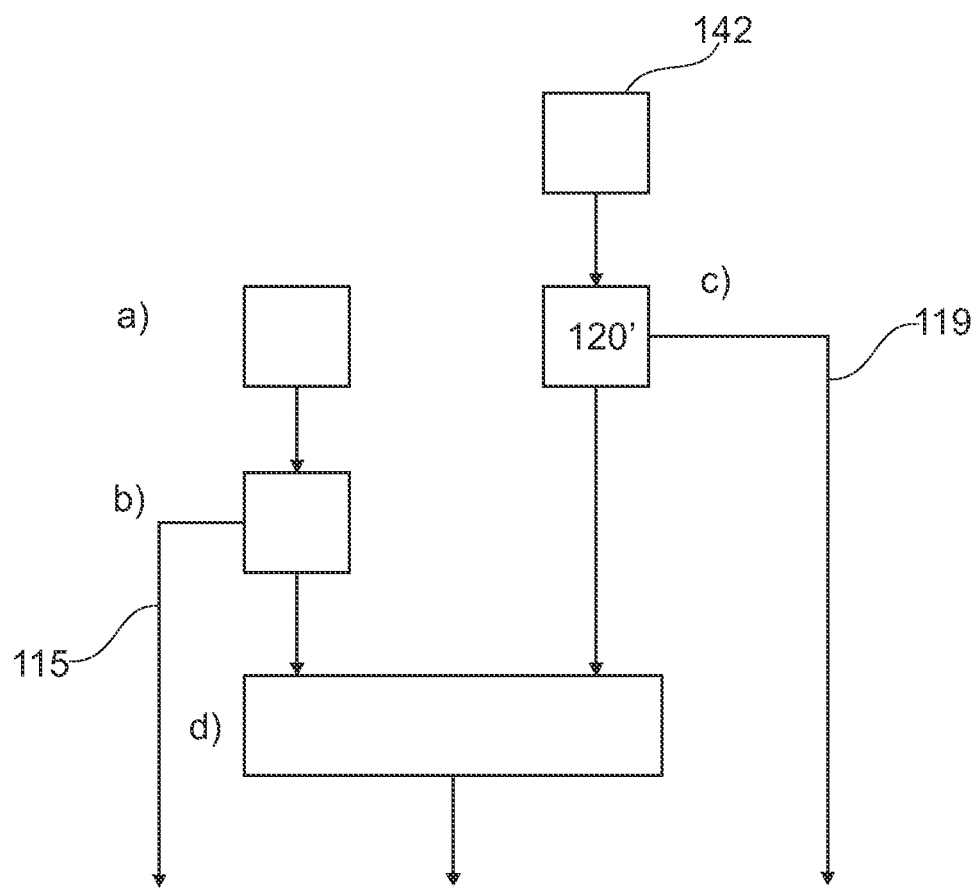
FIGS. 4 to 7 show further examples of methods according to the present invention.

As indicated in FIG. 4, according to a further example, the predetermined ablation profile 122 is adjustable in an adjustment step 142 by the user in its size, shape and/or location. This is indicated in FIG. 4 with reference numeral 120'. Further, the steps d) to f) may be repeated (not further shown) to provide updated information.

Figure 5:
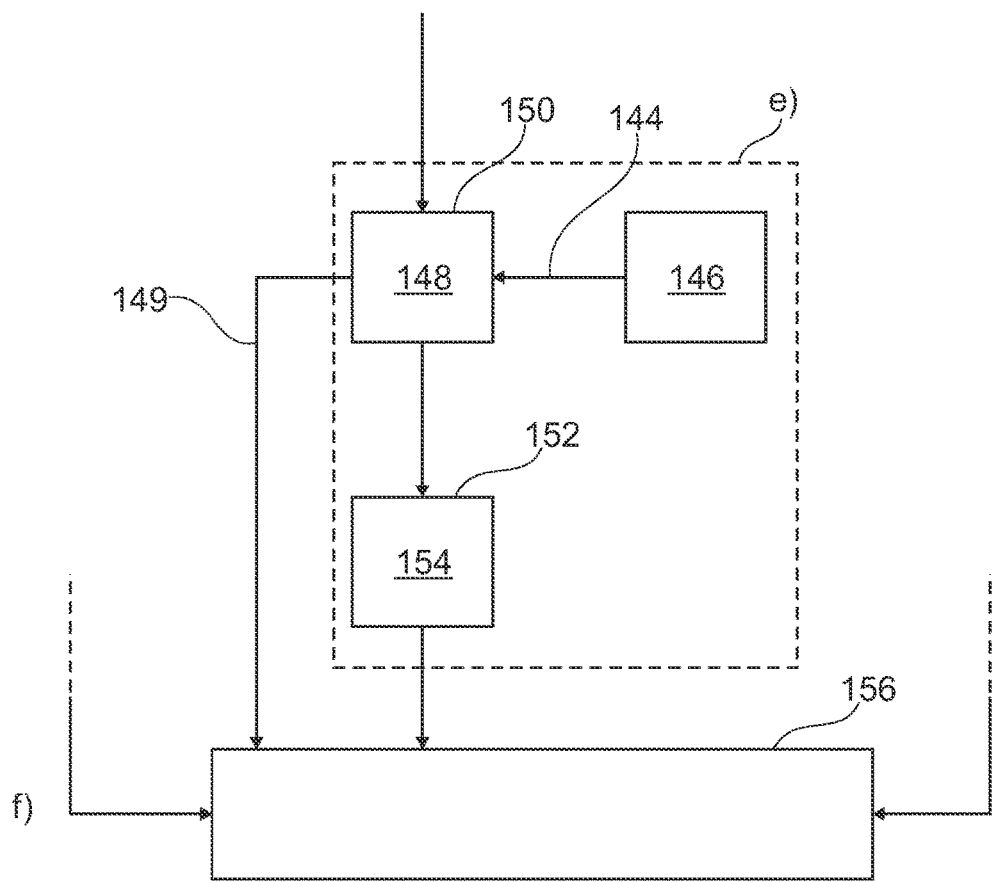

FIG. 5 shows a further example in which step e) comprises an addition 144 of a predetermined first safety margin 146 as the safety factor to the at least one segmented tumour to generate 150 a dilated contour of the tumour 148 in a generation step 150. Further, step e) also comprises displaying the dilated contour 148, as indicated with reference numeral 149. Next, in a determination step 152, the parts of the dilated contour 148 arranged outside the ablation profile are determined as critical dilated contour portions 154. Further, in step f), the critical dilated contour portions 154 are indicated in the display in an indication step 156.

For example, the critical dilated contour portions are indicated with a colour-coded profile (not shown).

Figure 6:
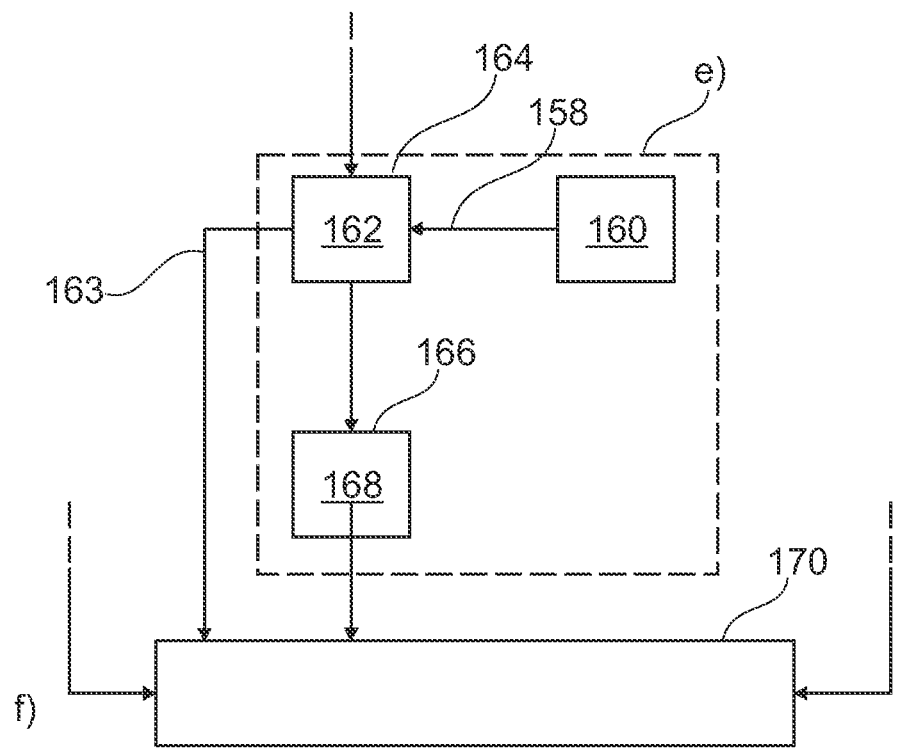

FIG. 6 shows a further example of a method according to the present invention, in which step e) comprises a subtraction 158 of a predetermined second safety margin 160 as the predetermined safety factor from the predetermined ablation profile to generate a limited planned ablation profile 162 in a generation step 164. The planned ablation profile 162 is displayed, as indicated with reference numeral 163. Further, in a determination step 166, the parts of the contour arranged outside the planned ablation profile are determined as critical contour portions 168. In step f), the critical contour portions are indicated in the display in an indication step 170.

For example, the critical contour portions are indicated with a colour-coded profile.

The ablation profile may graphically be displayed in a different way than the limited planned ablation profile. The segmented tumour may graphically be displayed in a first mode for areas/regions in which the planned ablation profile overlaps, and in second mode for areas/regions in which the planned ablation profile does not overlap. The first mode may differ from the second mode.

The segmented tumour may be displayed in an overlaid manner together with image data of a surrounding region (not further shown).

The image data may be X-ray image data, for example CT image data of a patient.

Figure 7:
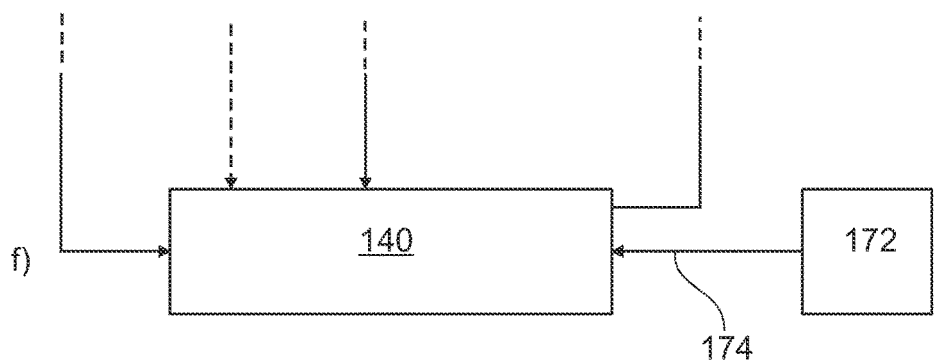

FIG. 7 shows an example in which a planned insertion path 172 of an ablation target for the tumour targeting ablation is shown together with the virtual planning ablation result 140, as indicated with arrow 174.

The indication of critical dilated contour portions and/or critical contour portions may comprise displaying the portions in a different graphical manner than the other, i.e. uncritical portions (not further shown).

The contour may be a contour line and the dilated contour may be a dilated contour line.

FIG. 8 shows a tumour cross-section contour in an entry point in FIG. 8B and in a progression view in FIG. 8A. Both figures show a background image 210 acquired by X-ray image acquisition, for example a CT-based projection of a 3D data set.

In FIG. 8A, 8B, a segmented lesion cross-sectional outline 212 is shown in two discriminating line types, with a first line type 214 and a second line type 216, which will be explained further below. Further, planned ablation isotherms 218 are shown. A first pattern 220 indicates a first isotherm, a second pattern 222 a second isotherm, and a third pattern 224 a third isotherm.

In FIG. 8A, the first isotherm 220 comprises two circular portions arranged in an overlapping manner, whereas the first isotherm 220 is shown in FIG. 8B in an ellipsoid form.

FIG. 8B further shows an insertion path 226 of an interventional device for performing the ablation, for example an ablation needle.

During the planning, the needle path and the ablation profile may be specified in a user-defined arbitrary viewing plane, by specifying the target and entry points of the applicator. An optimal ablation profile may then be selected among a number of stored ablation profiles. Additional ablation applicators may be specified using the same workflow. It is also possible to position applicators in parallel to a previous selected applicator by defining the target point only. As mentioned above, the isotherms representing the ablation zones are shown in cross-sections fused and blended on top of the image data. In this way, the ablation zones and the accompanied needle trajectories may be inspected at any plane position and orientation.

The tumour coverage feedback may be implemented in open GL by first rendering the destructive ablation profile in the (non-visible) stencil buffer. By using a stencil test, the cross-sectional outline may be rendered twice in different colours without overlapping the stencil buffer area. This is typically done by a code snippet as:

```
glEnable( GL_STENCIL_TEST );
SetContourColor(Vector3D(0.4, 1.0, 0.4));
glStencilOp(GL_KEEP, GL_KEEP, GL_KEEP);
glStencilFunc( GL_NOTEQUAL, 0,
CmodelAblation::STENCILMASK_ALL);
DrawContours( );
glStencilFunc( GL_EQUAL, 0,
CmodelAblation::STENCILMASK_ALL);
SetContourColor(Vector3D(1.0, 0.4, 0.4));
DrawContours( );
glDisable(GL_STENCIL_TEST );
```

Additional needles may be needed for complete coverage of the tumour. By browsing through the image cross-sections, the overlap may be inspected in all various plane positions and orientations. The planned ablation volume may be shown relatively to the segmented tumour volume in a volume rendering mode, as shown in top left corner of multi-view presentation in FIG. 9. The top left quadrant shows the specified isotherm of the ablation volume in a first colour 230, blended transparently over the tumour volume shown in a second colour 232.

Figure 10:
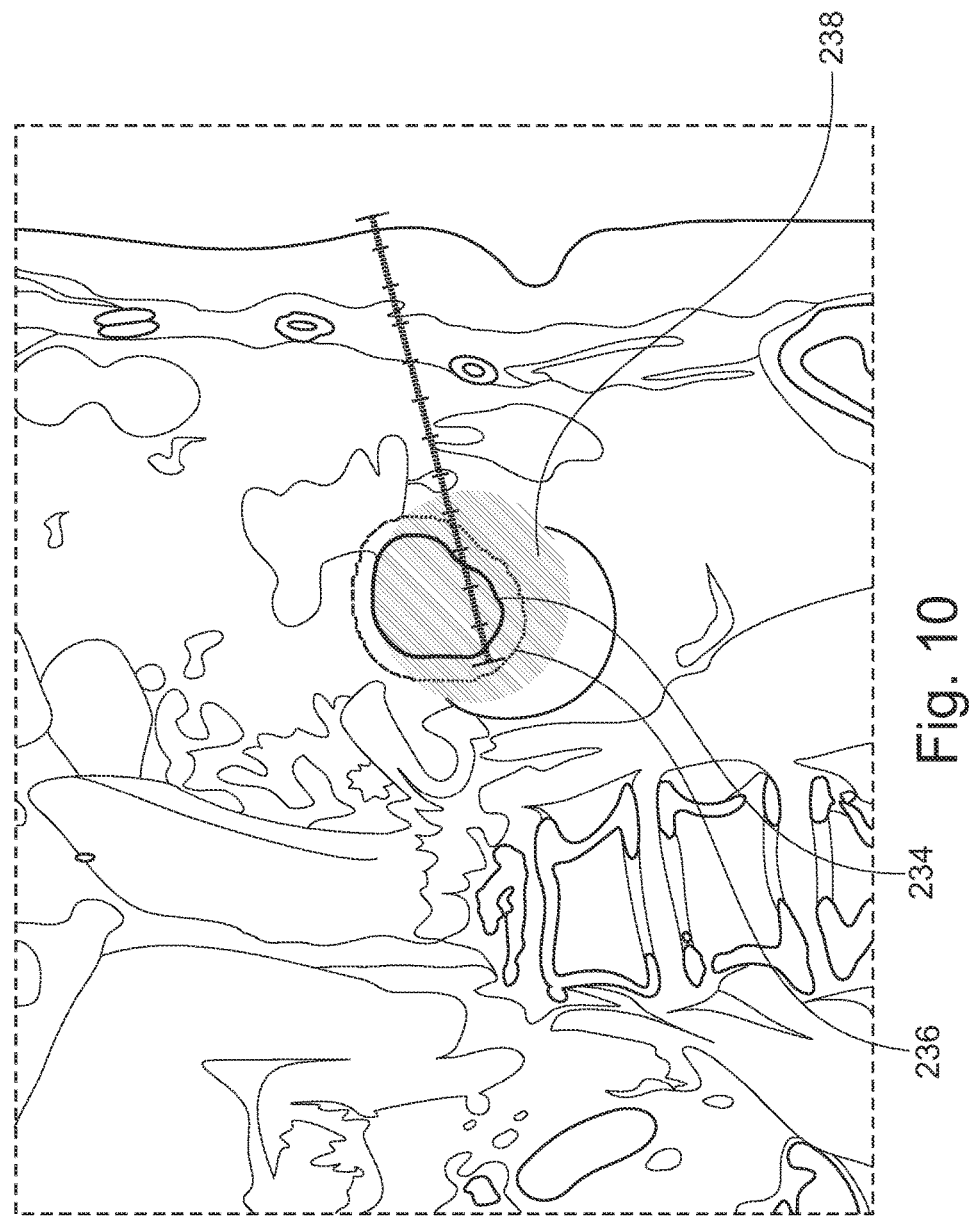
FIG. 10 shows a further example of a displayed virtual planning ablation result according to the present invention.

As mentioned above, successful ablation requires complete necrosis of the entire tumour as well as a margin around the lesion, for example a 0.5 to 1 cm margin. The margin may be added to the segmented tumour description, and the resulting volume may be referred to as planned target volume (PTV). The added margin hides/overrules the real location of the tumour boundary, which may be of importance in the neighbourhood of vessels (heat sink), where the safety margin may need to be relaxed. According to the present invention, two outlines are shown, a first outline 234 of the real segmented tumour, and a second contour 236 for the planned target volume (FIG. 10). The boundary of the segmented lesion, i.e. the first line 234, may be shown in a first colour, a user controllable transparent first pattern 238, for example a transparent red ellipse, indicates the planar cross-section with an overlapping ablation profile (not further shown).

In FIG. 10, the initial ablation profile would cover the tumour. By applying the safety factor to the tumour outline, according to the invention, a larger tumour outline is the result. This larger outline is now not fully covered by the ablation profile. Hence the respective indication by modifying the larger tumour outline.

As an addition to showing the overlap coverage with the dilated contour, it is also possible to determine, i.e. to calculate and to display, an overlap with the "real" tumour contour, i.e. with the contour prior to applying the safety factor.

Figure 11:
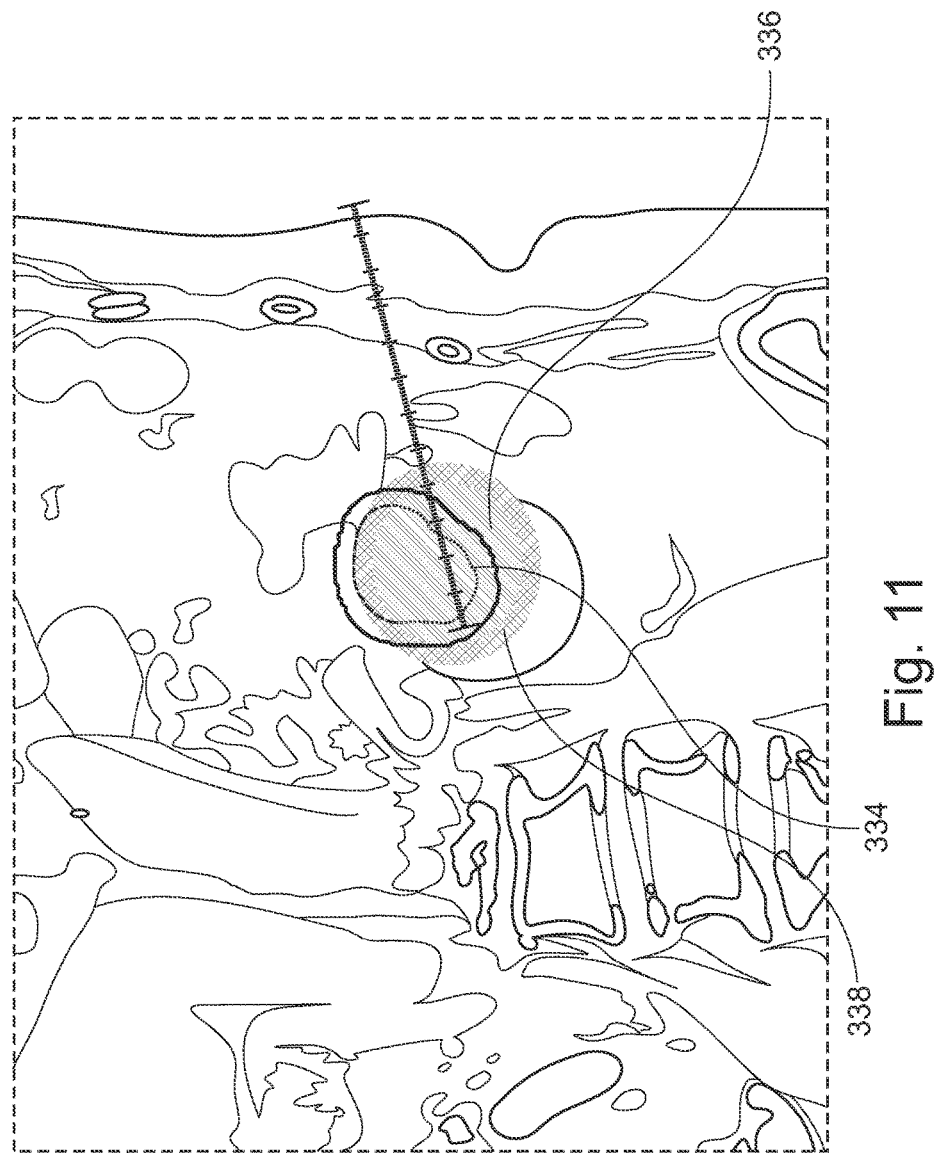
FIG. 11 shows a further example of a displayed virtual planning ablation result according to the present invention.

FIG. 11 shows an alternative approach, according to which a (possibly colour-coded) safety margin is included in the isotherms specification. By overlapping and colour-coding, a segmented lesion, arranged inside a first contra-line 334, with the inner ablation profiles, indicated with a first pattern 336, the outer ablation isotherm, indicated with a second pattern 338, will provide a safety margin. It is noted that in case of cryoablation, the outer zero degree isotherm, as provided by the applicator manufacturers, will provide a natural safety margin.

In FIG. 11, once again, the initial ablation profile would cover the tumour. By applying the safety factor to the ablation profile, according to the invention, a smaller ablation profile is the result. This smaller profile now does not fully cover the tumour. Hence the respective indication by the modification of the tumour outline.

Figure 9:
FIG. 9 shows a further example of a displayed virtual planning ablation result according to an exemplary embodiment of the present invention, in relation with further ablation planning information.

As indicated in FIG. 9, a first (zero degree) isotherm is used as mask in the colour-coded tumour boundary presentation.

Figure 12:
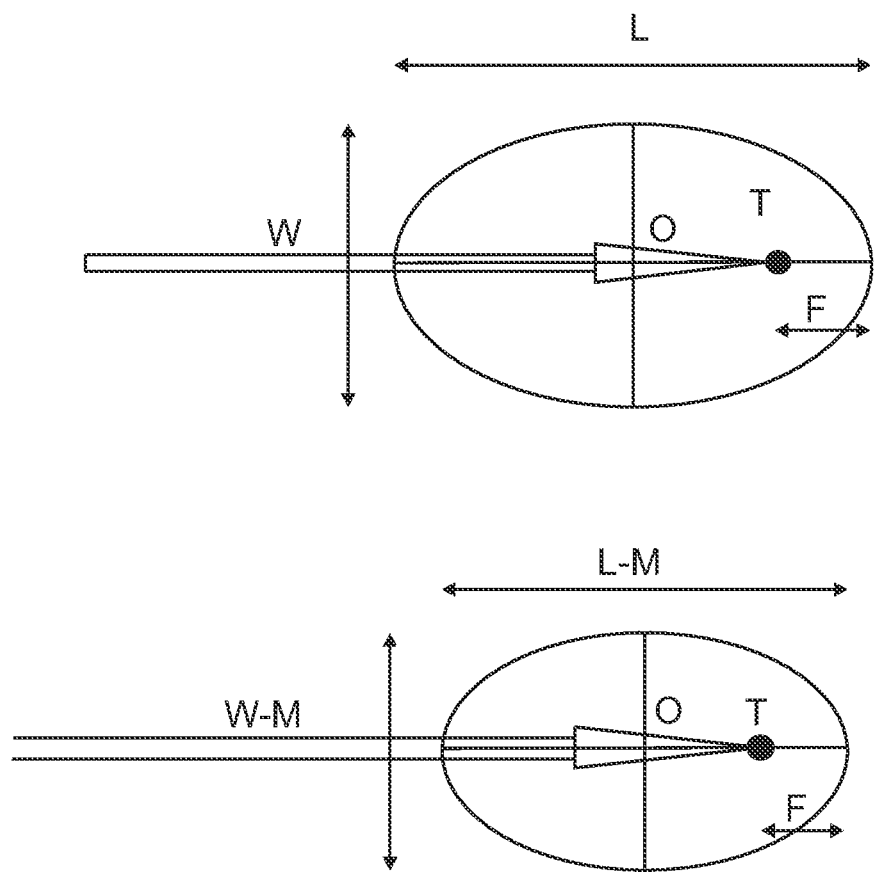
FIG. 12 shows further aspects in relation with the present invention.

With radiofrequency ablation or microwave ablation, only one elliptical ablation zone may be specified. By defining the safety margin, a second smaller concentric ablation profile can be constructed automatically as shown in FIG. 12 by the following observation.

The Origin (O) of an ellipsoid (L, W) ablation profile is defined relative to the Tip (T) of the applicator needle by the relation: O=T+F−L/2, where F is the Front of the ablation zone extending the Tip. A smaller ellipsoid (L−M, W−M) is defined by the relation O=T+$F_2$−(L−M)/2, where M is the safety margin. The ellipsoid can be made iso-centric using the equation: T+F−L/2=T+$F_2$−(L−M)/2→$F_2$=M/2.

As an example, the estimated size of the ablation zone created by means of three MWA valley Lab VT1237 percutaneous antennas that are activated at 45 W during 10 minutes at a distance of 20 mm is defined by an ellipsoid definition where L=55 mm, W=50 min and F=10 mm. So in this case the dimensions of the inner ellipsoid, with a 10 mm safety area will be: L=45 mm, W=40 mm and F=5 mm.

Figure 13:
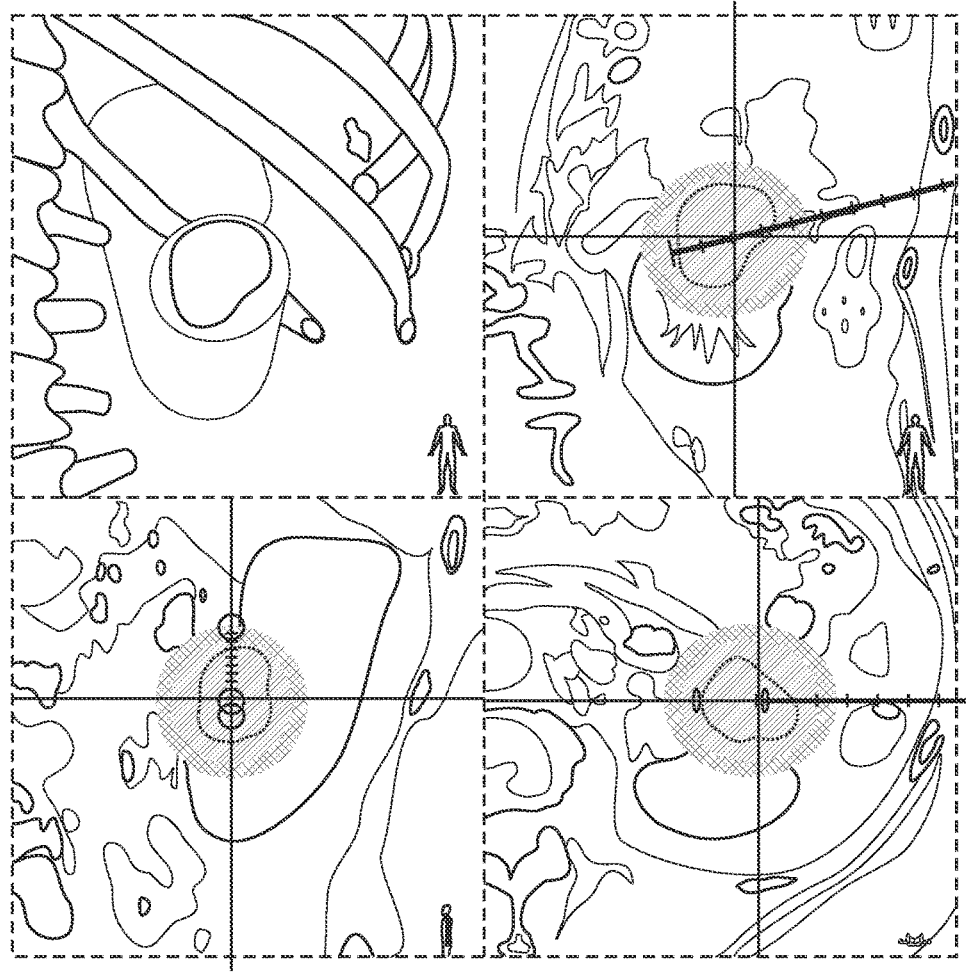
FIG. 13 shows a further example of a displayed virtual planning ablation result according to an exemplary embodiment of the present invention.
Figure 15:
Figure 16:
Figure 17:
Figure 18:
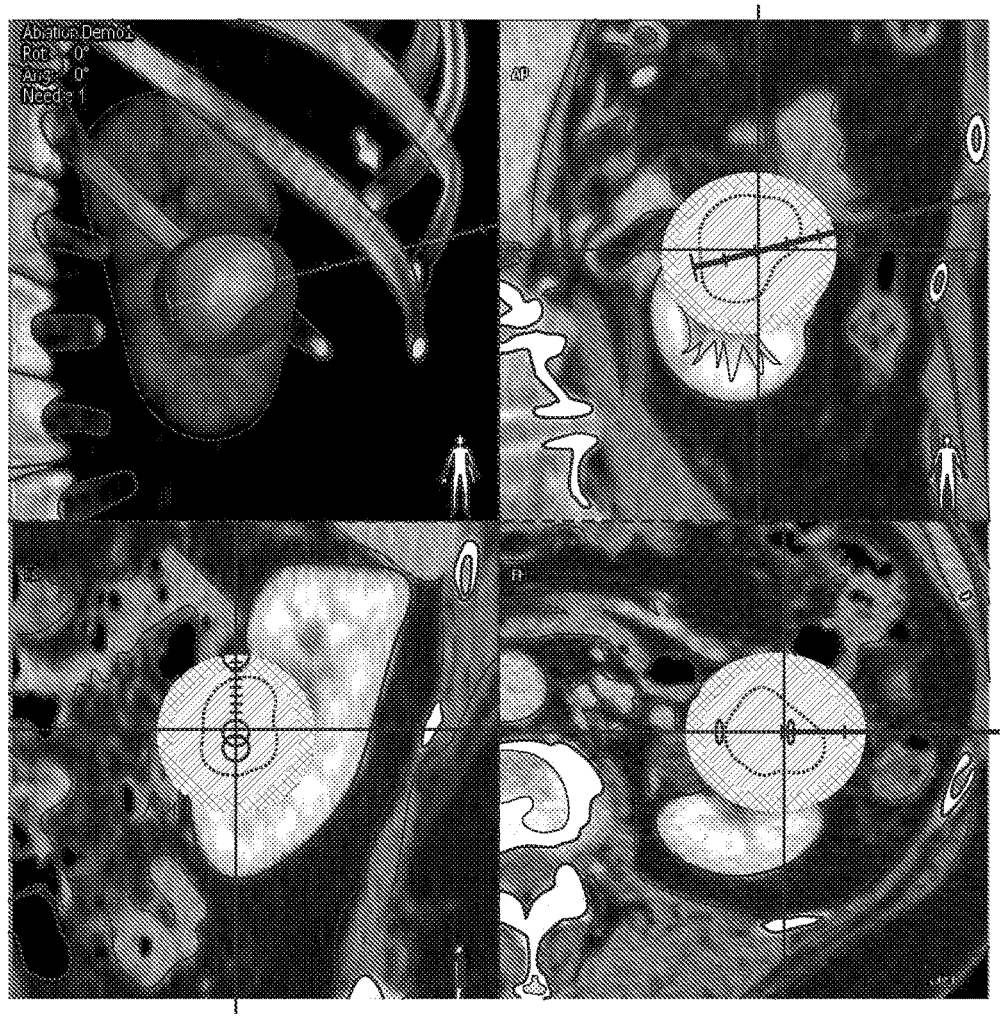

The image in FIG. 11 shows the use of this ablation profile. The inner outline shows the cross-section with a segmented lesion area. The outer outline displays the cross-section with the dilated PTV. It is noted, when comparing FIG. 11 and FIG. 10, that if the real tumour boundary is outside the inner ablation zone, indicated by means of a highlighted outline, the cross-section of the dilated tumour displayed in a first pattern will be outside the real predicted ablation. So instead of overlapping the dilated lesion with the predicted ablation zone, it is now to overlap the real lesion with the modified ablation profiles, and since the dilated lesion boundary has no real clinical value any more, it can be omitted. This is shown, for example, in a multi-view presentation of FIG. 13.

For better understanding, the drawings of FIGS. 8 to 11 and 13 are also shown with photographic images in FIGS. 14 to 18.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A planning device for tumour targeting ablation planning, comprising:
   a processing unit;
   an interface unit; and
   a display unit;
   wherein the interface unit is configured: to provide at least one segmented tumour in a 3D data set to be treated in an ablation procedure; and to provide a predetermined ablation profile;
   wherein the processing unit is configured to perform acts of:
      generating a contour of the at least one segmented tumour;
      overlapping the predetermined ablation profile with at least a part of the at least one segmented tumour to form an overlapping region;
      identifying the overlapping region;
      applying a predetermined safety factor to at least a part of the overlapping region to generate a modified overlapping region;
      determining parts of the overlapping region that are arranged outside the modified overlapping region as overlapping portions;
      applying a predetermined safety margin to the predetermined ablation profile to form a modified ablation profile, and
   wherein the display unit is configured: to display the contour of the at least one segmented tumour; to display the modified ablation profile and the predetermined ablation profile overlapped with the at least the part of the at least one segmented tumour in the overlapping region; and to display the overlapping portions in relation with the contour and the predetermined ablation profile as virtual planning ablation result.

2. The planning device according to claim 1, wherein the interface unit is configured for adjusting the predetermined ablation profile by a user in its size, shape and/or location to provide an adjusted predetermined ablation profile,
   wherein, based on the adjusted predetermined ablation profile, the processing unit is configured to repeat the acts of identification, application, and determination, and
   wherein, based on the adjusted predetermined ablation profile, the display unit is configured to provide updated ablation planning information.

3. The planning device according to claim 1, wherein the processing unit is configured: to add the predetermined safety margin to the at least one segmented tumour to generate a dilated contour of the tumour; and to determine parts of the dilated contour arranged outside the predetermined ablation profile as dilated contour portions, and
   wherein the display unit is configured: to display the dilated contour; and to indicate the dilated contour portions.

4. The planning device according to one of the claim 1, wherein the processing unit is configured: to subtract the predetermined safety margin from the predetermined ablation profile to generate a limited planned ablation profile; and to determine parts of the contour arranged outside the limited planned ablation profile as contour portions, and
   wherein the display unit is configured: to display the limited planned ablation profile; and to indicate the contour portions.

5. The planning device of claim 1, wherein the display unit is configured to display the at least one segmented tumour in a first mode for regions in which the modified ablation profile overlaps with the at least one segmented tumour, and in second mode for regions in which the modified ablation profile does not overlap with the at least one segmented tumour, the first mode being different from the second mode.

6. The planning device of claim 1, wherein the display unit is configured to display the predetermined ablation profile in a different way than the modified ablation profile.

7. The planning device of claim 1, wherein the display unit is configured to display the predetermined ablation profile with a first pattern and the predetermined safety margin with a second pattern which is different from the first pattern.

8. A medical system for tumour targeting ablation, comprising:
   an image acquisition unit;
   a planning device; and
   an ablation unit;
   wherein the planning device comprises;
      a processing unit;
      an interface unit; and
      a display unit;
   wherein the interface unit is configured: to provide at least one segmented tumour in a 3D data set to be treated in an ablation procedure; and to provide a predetermined ablation profile;
   wherein the processing unit is configured to:
      generate a contour of the at least one segmented tumour;
      overlap the predetermined ablation profile with at least a part of the at least one segmented tumour to form an overlapping region;
      identify the overlapping region;
      apply a predetermined safety factor to at least a part of the overlapping region to generate a modified overlapping region;
      determine parts of the overlapping region that are arranged outside the modified overlapping region as overlapping portions; and
      apply a predetermined safety margin to the predetermined ablation profile to form a modified ablation profile, and
   wherein the display unit is configured: to display the contour of the at least one segmented tumour; to display the modified ablation profile and the predetermined ablation profile overlapped with the at least the part of the at least one segmented tumour in the overlapping region; and to display the overlapping portions in relation with the contour and the predetermined ablation profile as virtual planning ablation result, wherein the image acquisition unit is configured to provide the 3D data set from which the tumour is segmented, wherein the planning device is configured to provide an ablation path, and wherein the ablation unit is configured to apply the ablation procedure to the tumour.

9. The medical system according to claim 8, wherein the image acquisition unit is an X-ray imaging device.

10. A method for tumour targeting ablation planning, comprising acts of:
a) providing at least one segmented tumour in a 3D data set to be treated in an ablation procedure;
b) generating and displaying a contour of the at least one segmented tumour;
c) providing and displaying a predetermined ablation profile to overlap with at least a part of the at least one segmented tumour to form an overlapping region;
d) identifying by a processor the overlapping region;
e) applying by the processor a predetermined safety factor to at least a part of the overlapping region to generate a modified overlapping region, wherein parts of the overlapping region arranged outside the modified overlapping region are determined as overlapping portions;
f) applying a predetermined safety margin to the predetermined ablation profile to form a modified ablation profile, and
g) displaying by a display a virtual planning ablation result including a display of the contour of the at least one segmented tumour; a display of the modified ablation profile and the predetermined ablation profile overlapped with the at least the part of the at least one segmented tumour in the overlapping region; and a display of the overlapping portions in relation with the contour and the predetermined ablation profile as virtual planning ablation result.

11. The method according to claim 10, wherein the predetermined ablation profile is adjustable by a user in its size, shape and/or location, and wherein the acts d) to g) are repeated to provide updated information.

12. The method according to claim 10, wherein the applying act comprises acts of:
adding a predetermined safety margin to the at least one segmented tumour to generate a dilated contour of the tumour;
displaying the dilated contour;
determining parts of the dilated contour arranged outside the predetermined ablation profile as dilated contour portions; and
wherein the displaying act displays the dilated contour portions in the display.

13. The method according to claim 12, wherein the displaying act displays the dilated contour portions and/or the contour portions in a different graphical manner than the other portions.

14. The method according to claim 10, wherein the applying act comprises acts of:
subtracting a predetermined safety margin from the predetermined ablation profile to generate a limited planned ablation profile;
displaying the limited planned ablation profile;
determining parts of the contour arranged outside the limited planned ablation profile as contour portions; and
wherein the displaying act displays the contour portions in the display.

15. The method according to claim 10, wherein the displaying act displays at least one segmented tumour in an overlaid manner together with image data of a surrounding region.

16. The method according to claim 10, wherein the displaying act displays a planned insertion path of an ablation target for the tumour targeting ablation.

17. A non-transitory computer readable medium comprising computer instructions for tumour targeting ablation planning, which, when executed by a processor, configure the processor to perform acts of:
providing at least one segmented tumour in a 3D data set to be treated in an ablation procedure;
generating and displaying a contour of the at least one segmented tumour;
providing and displaying a predetermined ablation profile to overlap with at least a part of the at least one segmented tumour;
identifying an overlapping region;
applying a predetermined safety factor to at least a part of the overlapping region to generate a modified overlapping region, wherein parts of the overlapping region arranged outside the modified overlapping region are determined as overlapping portions;
applying a predetermined safety margin to the predetermined ablation profile to form a modified ablation profile; and
displaying the overlapping portions in relation with the contour, the modified ablation profile and the predetermined ablation profile as virtual planning ablation result.

* * * * *